United States Patent [19]

Bunker et al.

[11] 4,452,810

[45] Jun. 5, 1984

[54] INSECT REPELLENT: N,N-DIETHYL-2-(4-THIOCHROMANYLOXY)-PROPIONAMIDE

[75] Inventors: Nathan S. Bunker, Martinez; Rayman Y. Wong, Richmond, both of Calif.

[73] Assignee: Stauffer Chemical Company, Westport, Conn.

[21] Appl. No.: 531,135

[22] Filed: Sep. 12, 1983

[51] Int. Cl.³ .................... C07D 327/00; A01N 43/02
[52] U.S. Cl. ........................................ 424/275; 549/23
[58] Field of Search ........................... 549/23; 424/275

[56] References Cited

U.S. PATENT DOCUMENTS 3,960,891  6/1976  Malen et al. ........................... 549/23

Primary Examiner—Alan Siegel
Attorney, Agent, or Firm—Joel G. Ackerman

[57] ABSTRACT

The compound N,N-diethyl-2-(4-thiochromanyloxy)-propionamide,

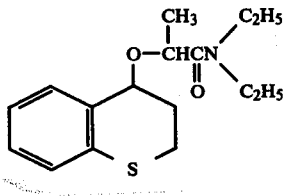

is an insect repellent.

4 Claims, No Drawings

INSECT REPELLENT: N,N-DIETHYL-2-(4-THIOCHROMANYLOXY)-PROPIONAMIDE

This invention relates to the novel compound N,N-diethyl-2-(4-thiochromanyloxy)-propionamide having the formula

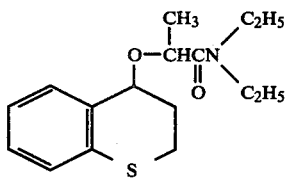

As will be shown from the data which follows, this compound has been found to have utility as an insect repellent, particularly for repelling flying insects, and most particularly, houseflies, from lighting and/or feeding.

The novel compound can be prepared by reaction of thiochroman-4-ol with an N,N-diethyl-2-halopropionamide in the presence of an appropriate solvent and sodium hydride in the sodium salt, according to the reaction

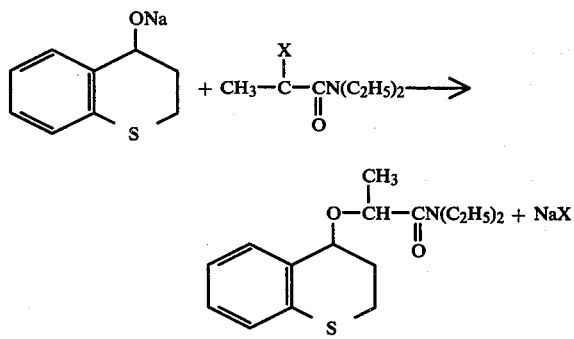

in which X is chlorine or bromine.

EXAMPLE

The following represents an example of the preparation of the subject compound.

In a flask equipped with a stirrer and argon blanket, there was placed 0.8 grams (g) (0.033 mole) sodium hydride in a 50% oil dispersion. The sodium hydride was washed with tetrahydrofuran and dried under vacuum, then suspended in 20 milliliters (ml) dimethylformamide. To this solution there was then added, with stirring, a solution of 5.2 g (0.031 mole) thiochroman-4-ol in 30 ml dimethylformamide, during which time vigorous evolution of gas was observed. The mixture was then stirred for one hour, cooled to 0° C., and there was then added 5.2 g (0.032 mole) N,N-diethyl-2-chloropropionamide at a rate so as to maintain the temperature at a maximum of 15° C.

When the addition of the amide was complete, the mixture was warmed to room temperature, the argon inlet was replaced with a drying tube, and the mixture was allowed to stir overnight.

There was then added 25 ml water, the mixture was transferred to a separatory funnel, diluted with additional 75 ml water and extracted with ten 10-ml portions of methylene chloride. The extracts were combined, washed with water and saturated sodium chloride solution, and dried over sodium sulfate. The dried solution was filtered and dried under vacuum to remove the solvents. There was obtained 9.1 g (99% of theoretical yield) of a clear, dark, yellowish-brown oil. This product was subsequently treated by high pressure liquid chromatography to produce a clear yellow oil, $n_D^{30}$ 1.5427.

Structure of the product was confirmed by infrared, nuclear magnetic and mass spectroscopy.

Insect Repellency Evaluation

Houseflies

The insect utilized for this test was the housefly, *Musca domestica* (L.). One hundred houseflies of mixed sexes were placed in test cages. In each cage was placed a sugar cube saturated with 1.0 ml of acetone containing various amounts (by weight) of the test compound. The cube was dried and weighed before being placed in the cage. Each cage also contained a water-saturated cotton plug to provide moisture. The test cages were placed on a turntable and rotated at 1.5 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube containing only acetone and no test compound, was calculated. The lower the repellency ratio, the greater the repellency of the test compound. The repellency ratios of the test compound at different concentrations are shown in the following Table.

TABLE

| Test Compound wt. % | Repellency Ratio |
|---|---|
| 1.0 | 0.14 |
| 1.0 | 0.18 |
| 0.5 | 0.37 |
| 0.25 | 0.60 |
| 0.1 | 0.66 |
| 0.1 | 0.68 |
| 0.1 | 0.69 |
| 0.01 | 1.00 |
| 0.01 | 1.00 |

Thus, the test compound was effective as an insect repellent at concentrations as low as 0.1 weight %, with the repellency activity increasing as concentration increased in the acetone solution. At a concentration of only 1.0 weight %, the repellency ratio was between 0.14 and 0.18, which indicates that the weight loss of the sugar cube was approximately one-sixth to one-seventh that of the untreated sugar cube (contracted with acetone only).

The novel compound of this invention may be used as an insect repellent in either diluted or undiluted form. When used in a diluted form, compositions may contain relatively high or relatively low concentrations of the active compound. For example, the active compound can be incorporated into relatively high concentration compositions such as wet sprays or solutions in alcohol or other suitable solvents. Such compositions may contain, in addition to the active compound, adjuvants such as emulsifying agents, surface-active agents, anti-oxidants and propellants which may be normally found in insect repellent preparations. The active compound of this invention may be employed as the sole active component of such compositions or may be used in admixture with other compounds having a similar or different utility. For example, the compound may be incorporated into creams, lotions, powders, suntan oil, insecticides and other preparations which may contain pesticidal or other useful substances, as well as into compositions of various types used for treating fabrics or articles of clothing to render them insect repellent. In general, compositions for repellent use may contain from 0.1 up to 95 weight %, preferably from 1 to about 40 weight %, of the novel compound. High concentration formulations, containing up to 95% of the compound, could also be utilized for low-volume spraying from the air.

Examples of typical formulations employing the compound of this invention are for instance,

EXAMPLE 1

Emulsifiable Concentrate

| Component | Weight % |
|---|---|
| Active Compound | 53.6 |
| Aromatic Hydrocarbon Solvent | 36.4 |
| Emulsifier | 10.0 |
| Total | 100.0 |

EXAMPLE 2

Lotion

| Component | Weight % |
|---|---|
| Active Compound | 10.7 |
| Lanolin | 4.8 |
| Mineral Oil | 8.0 |
| Trihydroxyethylamine stearate | 1.8 |
| Glycosterin | 0.8 |
| Glycerine | 4.6 |
| Sodium Benzoate | 1.0 |
| Water | 68.3 |
| Total | 100.0 |

EXAMPLE 3

Alcohol Solution

| Component | Weight % |
|---|---|
| Active Compound | 53.6 |
| Isopropanol | 46.4 |
| Total | 100.0 |

EXAMPLE 4

Alcohol Solution

| Component | Weight % |
|---|---|
| Active Compound | 80.0 |
| Ethanol | 20.0 |
| Total | 100.0 |

EXAMPLE 5

Wettable Powder

| Component | Weight % |
|---|---|
| Active Compound | 26.9 |
| Hydrated Calcium Silicate | 62.1 |
| Sodium Lignosulfonate | 5.0 |
| Orzan A (mixture of ammonium lignosulfonate and wood sugars) | 5.0 |
| Wetting Agent | 1.0 |
| Total | 100.0 |

What is claimed is:

1. A compound having the formula

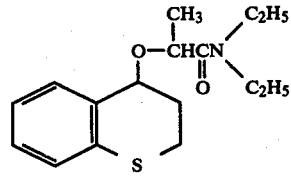

2. An insect repelling composition containing an amount of a compound having the formula

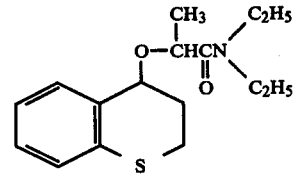

effective to repel insects from lighting or feeding and an inert diluent or carrier suitable for insect repellent compositions.

3. A method for repelling insects comprising applying to a locus to be protected from insects, an amount of a compound having the formula

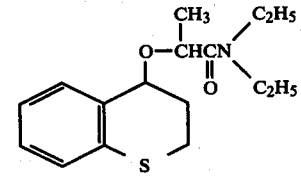

effective to repel insects from said locus.

4. A method according to claim 3 in which the insect is housefly.

* * * * *